US 6,528,195 B1

United States Patent
Taniguchi

(10) Patent No.: US 6,528,195 B1
(45) Date of Patent: Mar. 4, 2003

(54) MIXED IONIC CONDUCTOR AND DEVICE USING THE SAME

(75) Inventor: Noboru Taniguchi, Osaka (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/506,122

(22) Filed: Feb. 17, 2000

(30) Foreign Application Priority Data

Feb. 17, 1999 (JP) .............................. 11-038369

(51) Int. Cl.[7] ..................... H01M 8/10; G01N 27/407
(52) U.S. Cl. ..................... 429/33; 252/62.2; 204/421
(58) Field of Search .......................... 429/30, 33, 188, 429/304; 252/62.2; 204/421

(56) References Cited

U.S. PATENT DOCUMENTS 5,387,330 A    2/1995   Taniguchi et al.

FOREIGN PATENT DOCUMENTS

| EP | 0 677 741 | 10/1995 |
|---|---|---|
| JP | 5-28820 | 2/1993 |
| JP | 5-234604 | 9/1993 |
| JP | 5-290860 | 11/1993 |
| JP | 6-223857 | 8/1994 |
| JP | 6-231611 | 8/1994 |
| JP | 6-290802 | 10/1994 |
| JP | 7-65839 | 3/1995 |
| JP | 7-136455 | 5/1995 |
| JP | 8-29390 | 2/1996 |
| JP | 8-162121 | 6/1996 |
| JP | 8-198670 | 8/1996 |
| JP | 8-220060 | 8/1996 |
| JP | 8-327592 | 12/1996 |
| JP | 9-27330 | 1/1997 |
| JP | 9-295866 | 11/1997 |

OTHER PUBLICATIONS

Ryu et al. ("Chemical stability and proton conductivity of doped BaCe3–BaZrO3 solid solutions," Solid State Ionics 125 (Oct. 1999), pp. 355–367).*

HCA abstract of the Ryu et al. reference ("Chemical stability and proton conductivity of doped BaCe3–BaZrO3 solid solutions," Solid State Ionics 125 (Oct. 1999), pp. 355–367).*

Weinstroer et al., "Investigation of the influence of zirconium substitution on the properties of neodymium–doped barium cerates", Solid State Ionics, vol. 101–103 (1997) pp. 1113–1117, No Month Available.*

European Search Report—Application No. EP 00301251 dated Jul. 21, 2000.

* cited by examiner

Primary Examiner—Carol Chaney
Assistant Examiner—Susy Tsang-Foster
(74) Attorney, Agent, or Firm—Merchant & Gould P.C.

(57) ABSTRACT

A mixed ionic conductor with an ion conductive oxide has a perovskite structure of the formula $Ba_dZr_{1-x-y}Ce_xM_y^3O_{3-\gamma}$ wherein $M^3$ is at least one element selected from the group consisting of Sm, Eu, Gd, Tb, Yb, Y, Sc, and In; with $0.98 \leq d \leq 1$; $0.01 \leq x < 0.5$; $0.01 \leq y \leq 0.3$; $(2+y-2d)/2 \leq \gamma < 1.5$. Such a mixed ionic conductor has not only the necessary conductivity for electrochemical devices such as fuel cells, but also superior moisture resistance.

6 Claims, 3 Drawing Sheets

MIXED IONIC CONDUCTOR AND DEVICE USING THE SAME

BACKGROUND OF THE INVENTION

1. Field of the Invention

The present invention relates to a mixed ionic conductor and an electrochemical device, such as a fuel cell or a gas sensor, using the same.

2. Description of the Prior Art

The applicant has long been actively developing mixed conductors of protons and oxide ions (see for example Publication of Unexamined Japanese Patent Application (Tokkai) No. H5-28820 or H6-231611). These mixed ionic conductors are basically perovskite oxides containing barium and cerium wherein a portion of the cerium has been substituted by the substitute element M, so as to achieve a high ionic conductivity (chemical formula: $BaCe_{1-p}M_pO_{3-\alpha}$). Especially, when the substitution amount p of the substitution element M is 0.16 to 0.23, the mixed ionic conductor has a high conductivity, higher even than zirconia-based oxides (YSZ: yttrium-stabilized zirconia), which conventionally have been used as oxide ionic conductors. As the substitution element M, rare earth elements are suitable, in particular heavy rare earth elements, because of their atomic radius and charge balance.

New fuel cells, sensors and other electrochemical devices using such materials as a solid electrolyte have been developed. The sensor characteristics and the discharge characteristics of fuel cells using such materials have been shown to be superior to prior devices. Other patent applications related to these materials are Tokkai H5-234604, Tokkai H5-290860, Tokkai H6-223857, Tokkai H6-290802, Tokkai H7-65839, Tokkai H7-136455, Tokkai H8-29390, Tokkai H8-162121, and Tokkai H8-220060.

However, these materials show some problems with regard to their chemical stability. For example, barium tends to precipitate in $CO_2$ gas. To solve these problems, the applicant has proposed a counter-strategy in Tokkai H9-295866. However, even this counter-strategy is not perfect, and for example at low temperatures of 85° C. and 85% humidity, precipitation can be observed in shelf tests and boiling tests in water. Moreover, under high water vapor pressures as during discharge of the fuel cells, barium can be seen to precipitate near the platinum electrodes. Furthermore, with gas sensors, there is the problem of maintaining high ion conductivity at lower temperatures over a long time and the problem of raising the acid resistance of the oxide itself.

SUMMARY OF THE INVENTION

To solve these problems, it is an object of the present invention to improve the chemical stability of the mixed ionic conductors.

The main cause for decomposition of the oxides due to humidity is believed to be the fact that the segregated barium turning into barium hydroxide reacts with the carbon dioxide, and forms stable barium carbonate. To increase the moisture resistance, the present invention uses a mixed ionic conductor including the following perovskite structure oxide.

A mixed ionic conductor of one embodiment of the present invention (a first ionic conductor) includes an ion conductive oxide having a perovskite structure of the formula $Ba_a(Ce_{1-b}M^1{}_b)L_cO_{3-\alpha}$, wherein $M^1$ is at least one trivalent rare earth element other than Ce;

L is at least one element selected from the group consisting of Zr, Ti, V, Nb, Cr, Mo, W, Fe, Co, Ni, Cu, Ag, Au, Pd, Pt, Bi, Sb, Sn, Pb and Ga;

with $0.9 \leq a \leq 1$;

$0.16 \leq b \leq 0.26$;

$0.01 \leq c \leq 0.1$;

and $(2+b-2a)/2 \leq \alpha < 1.5$.

In this mixed ionic conductor it is preferable that $M^1$ is at least one element selected from the group consisting of La, Pr, Nd, Pm, Sm, Eu, Gd, Tb, Dy, Ho, Er, Tm, Yb, Y and Sc. More preferably, $M^1$ is Gd and/or Y.

It is also preferable that L is at least one element selected from the group consisting of Zr, Ti, Fe, Co, Ni, Cu, Bi, Sn, Pb and Ga. More preferably, L is at least one element selected from the group consisting of Zr, Ti, Bi, Pb and Ga.

A mixed ionic conductor of another embodiment of the present invention (a second ionic conductor) includes an ion conductive oxide having a perovskite structure of the formula $Ba_eZr_{1-z}M^2{}_zO_{3-\beta}$, wherein $0.9 \leq e \leq 1$;

$M^2$ is at least one element selected from the group consisting of trivalent rare earth elements, Bi, Ga, Sn, Sb and In;

with $0.01 \leq z \leq 0.3$;

and $(2+z-2e)/2 \leq \beta < 1.5$.

In this mixed ionic conductor it is preferable that $0.16 \leq z \leq 0.3$. It is also preferable that $M^2$ is at least one element selected from the group consisting of trivalent rare earth elements and In, especially elements selected from the group consisting of Pr, Eu, Gd, Yb, Sc and In.

A mixed ionic conductor of yet another embodiment of the present invention (a third ionic conductor) includes an ion conductive oxide having a perovskite structure of the formula $Ba_dZr_{1-x-y}Ce_xM^3{}_yO_{3-\gamma}$ wherein $M^3$ is at least one element selected from the group consisting of trivalent rare earth elements, Bi and In;

with $0.98 \leq d \leq 1$;

$0.01 \leq x \leq 0.5$;

$0.01 \leq y \leq 0.3$;

and $(2+y-2d)/2 \leq \gamma < 1.5$.

In this third mixed ionic conductor, it is preferable that $M^3$ is at least one element selected from the group consisting of Nd, Sm, Eu, Gd, Tb, Yb, Y, Sc and In. More preferably, $M^3$ is at least one element selected from the group consisting of Gd, In, Y and Yb.

The mixed ionic conductors of the present invention have not only the necessary conductivity for electrochemical devices such as fuel cells, but also superior moisture resistance.

Throughout this specification, "rare earth element" means Sc, Y, and the lanthanides (elements 57La through 71Lu). In the above formulas, $\alpha$, $\beta$ and $\gamma$ are determined by the absent amount of disproportionate oxygen.

The present invention also provides devices using such a mixed ionic conductor. A fuel cell in accordance with the present invention includes as a solid-state electrolyte a mixed ionic conductor as described above. A gas sensor in accordance with the present invention includes as a solid-state electrolyte a mixed ionic conductor as described above. Using the mixed ionic conductors of the present invention provides electric devices, such as fuel cells and gas sensors, with high moisture resistance, high performance, and long lifetimes.

DESCRIPTION OF THE PREFERRED EMBODIMENTS

The following is an explanation of the preferred embodiments of the present invention.

As the applicant has pointed out in the above-noted publications, the high conductivity of mixed ionic conductors in accordance with the present invention stems from the mixed ion conductivity of oxygen ions and protons. In order to improve the moisture resistance of such mixed ionic conductors, a suitable substitute element is introduced into the above-mentioned first ionic conductor so as to reduce the amount of barium in the perovskite oxide to less than the stochiometric ratio. In the following, such a mixed ionic conductor also is referred to as "additive system" conductor.

The second and the third ionic conductors in accordance with the present invention are also mixed ionic conductors with high moisture resistance. In the following, these mixed ionic conductors are referred to as "barium-zirconium system" conductors and "barium zirconium cerium system" conductors, respectively. While these systems are mixed ionic conductors exhibiting proton conductivity, they still provide high moisture resistance.

These systems of mixed ionic conductors can be obtained with conventional raw materials and manufacturing methods. Specific examples of manufacturing methods are explained along with the examples further below.

The following is an explanation of a device using a mixed ionic conductor in accordance with the present invention.

Figure 1:
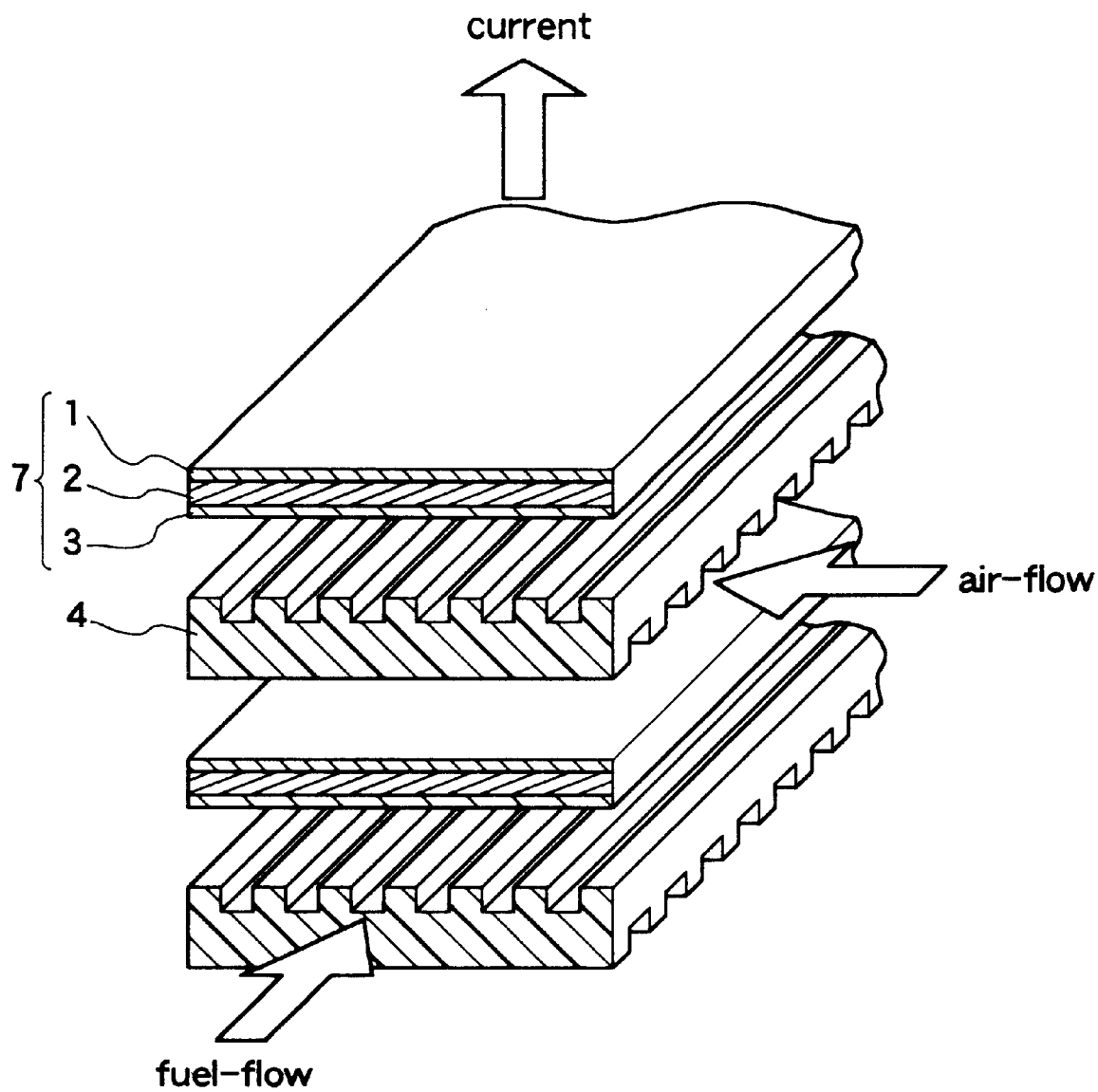
FIG. 1 is an exploded perspective cross-sectional view of an embodiment of a fuel cell using a mixed ionic conductor in accordance with the present invention.

FIG. 1 is a cross-sectional perspective view of an embodiment of a fuel cell in accordance with the present invention. This planar fuel cell has several layered units 7, which include a cathode (fuel electrode) 3, a solid electrolyte 2 layered on the cathode 3, and an anode (air electrode) 1 on the solid electrolyte 2. Separators 4 are arranged between the layered units 7.

When generating power, an oxidation gas 6 (such as air) is supplied to the anodes 1, and a fuel gas 5 (a reduction gas such as hydrogen or natural gas) is supplied to the cathodes 3. The oxidation-reduction reaction at the electrodes generates electrons, so that the fuel cell serves as an electric power source.

Figure 2:
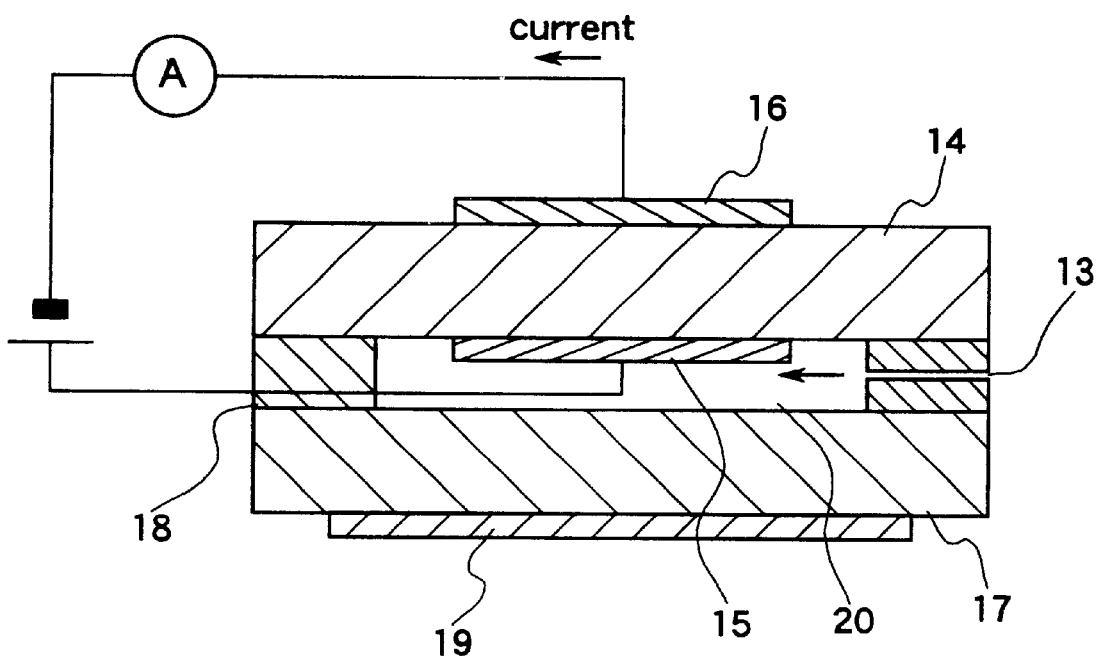
FIG. 2 is a cross-sectional view of an embodiment of a gas sensor using a mixed ionic conductor in accordance with the present invention.

FIG. 2 is a cross-sectional view of an embodiment of a gas sensor in accordance with the present invention. This HC sensor (hydrocarbon sensor) includes an anode 15, a solid electrolyte 14 on the anode 15, and a cathode 16 on the solid electrolyte 14. This layered structure is attached with an inorganic adhesive 18 to a (ceramic) substrate 17, providing a space 20 between the substrate and the layered structure. This space 20 is in communication with the outside via a diffusion limiting hole 13.

When a certain voltage (for example 1.2V) is applied steadily between the two electrodes 15 and 16, a current that is proportional to the concentration of hydrocarbons in the space adjacent to the anode 15 is attained as output. During the measurement, the sensor is kept at a certain temperature with a heater 19 attached to the substrate. To provide the diffusion limiting hole 13 is advantageous to limit the inflow of the material to be measured (here, hydrocarbons) into the space 20.

This embodiment has been explained for a HC sensor, but an oxygen sensor is also possible by exchanging anode and cathode in the structure shown in FIG. 2. Furthermore, the mixed ionic conductor of the present invention is not limited the above, but also can be applied to all kinds of other electrochemical devices.

EXAMPLES

The following is a more detailed description of specific examples of the present invention. It should be noted that the present invention is in no way limited to these examples.

As examples of the present invention, oxides as shown in Tables 1 to 6 have been synthesized. These oxides were synthesized by solid state sintering. An oxide powder of barium, cerium, zirconium, and rare earth elements was weighed to the composition ratio listed in the tables, and crushed and mixed with ethanol in an agate mortar. After sufficient mixing, the solvent was removed, defatted with a burner, and crushing and mixing were repeated in the agate mortar. Then, the samples were pressed into columnar shape and fired for 10 hours at 1300° C. After the firing, granules of about 3 $\mu$m were produced by coarse crushing, with further crushing in a benzene solution with a planetary ball mill. The resulting powder was vacuum-dried at 150° C., and columns were formed with a hydrostatic press at 2 tons/cm$^2$, which were immediately fired for 10 hours at 1650° C. to synthesize a sintered product. For almost all samples, a very compact single-phase perovskite oxide was attained. The resulting samples were then evaluated as follows:

Boiling Test

As an accelerated test of moisture resistance, the samples were introduced into boiling water of 100° C., and the level of Ba precipitation was evaluated after 10 hours by measuring the pH value. This evaluation utilizes the fact that the pH value in the aqueous solution rises proportionally with the precipitation of barium. For a pH change of not more than 2, the moisture resistance was taken to be excellent (A), for more than 2 and not more than 3.5, it was taken to be good (B), for more than 3.5 and not more than 4, it was taken to be adequate (C), and for more than 4, it was taken to be poor (D).

Conductivity

After the above-mentioned boiling test, disks of 0.5 mm thickness and 13 mm diameter were made of the columnar sintered product samples, both sides of the disks were coated with a platinum paste on an area of 0.5 cm$^2$ each, which was baked onto the samples, and the ion conductivity was measured. In this experiment, the conductivity was calculated from the resistance with the alternating current impedance method in air. The measurement temperature was 500° C. The resistance of the leads of the measurement device was subtracted. When the conductivity (in S/cm) was at least 0.007, it was taken as A, for at least 0.001 and less than 0.007 it was taken as B, and for less than 0.001 it was taken as C.

Figure 3:
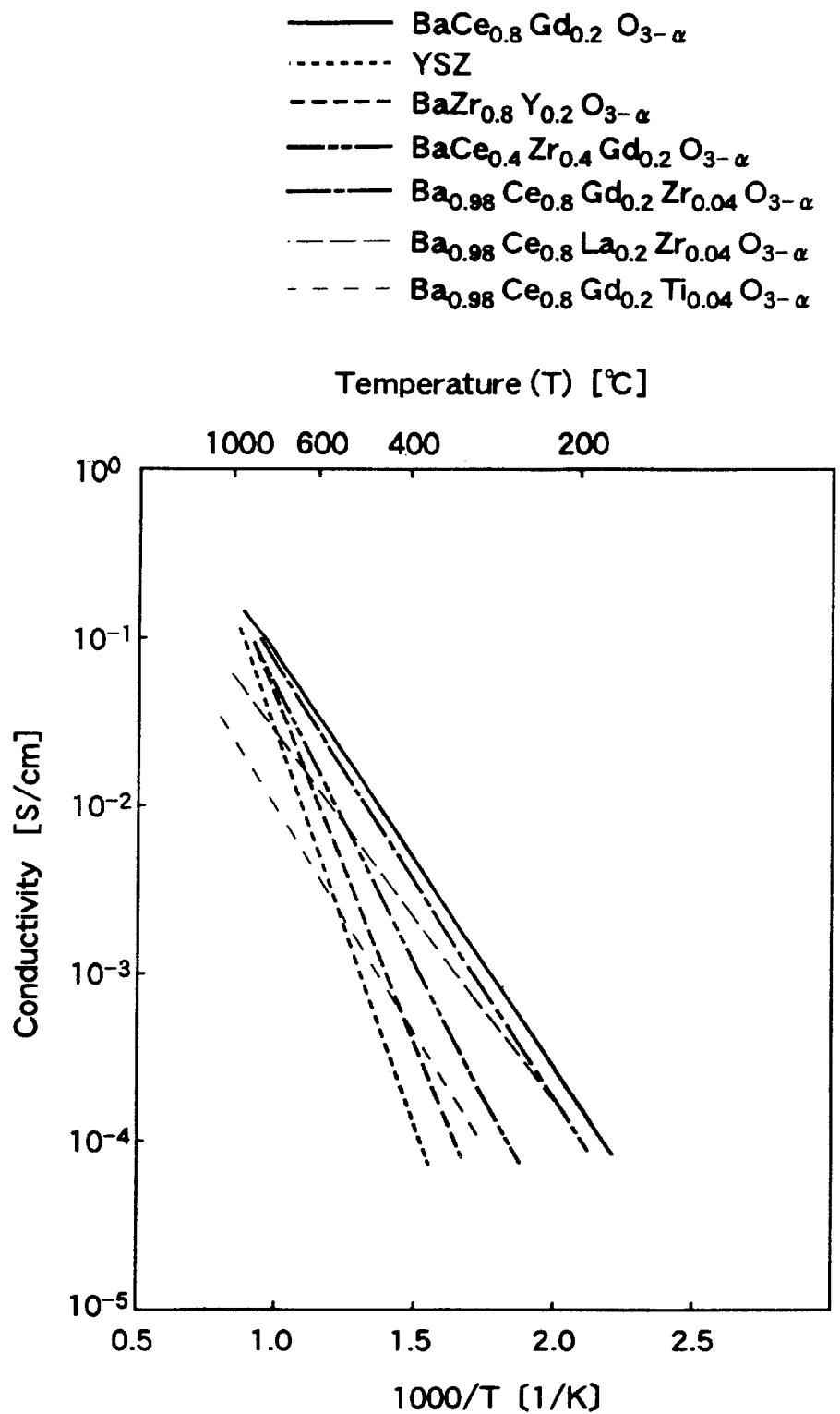
FIG. 3 is a graph showing the conductivity of mixed ionic conductors in accordance with the present invention.

FIG. 3 is an arrhenius plot showing the conductivity of materials in accordance with the present invention.

Crystallinity

When the sintered product was single-phase it was taken as A, when it was multi-phase, it was taken as B, and sintering failures were taken as C.

The tables show the conductivity at 500° C. and the result of the pH evaluation in the boiling test.

TABLE 1

| Material | Boiling Test | Crystallinity | Conductivity |
|---|---|---|---|
| $BaCe_{0.8}Gd_{0.2}O_{3-\alpha}$ | D | A | A |
| $Ba_{0.99}Ce_{0.8}Gd_{0.2}O_{3-\alpha}$ | D | A | A |
| $Ba_{0.98}Ce_{0.8}Gd_{0.2}O_{3-60}$ | D | A | A |
| $Ba_{0.94}Ce_{0.8}Gd_{0.2}O_{3-\alpha}$ | D | A | B |
| $Ba_{0.90}Ce_{0.8}Gd_{0.2}O_{3-\alpha}$ | D | A | B |

TABLE 2

Additive System

| Material | Boiling Test | Crystallinity | Conductivity |
|---|---|---|---|
| $BaCe_{0.8}Gd_{0.2}Zr_{0.01}O_{3-\alpha}$ | B | A | A |
| $BaCe_{0.8}Gd_{0.2}Zr_{0.4}O_{3-\alpha}$ | B | A | A |
| $BaCe_{0.8}Gd_{0.2}Zr_{0.60}O_{3-\alpha}$ | B | A | A |
| $BaCe_{0.8}Gd_{0.2}Zr_{0.1}O_{3-\alpha}$ | B | A | A |
| $BaCe_{0.8}Gd_{0.2}Zr_{0.11}O_{3-\alpha}$ | D | B | not measured |
| $BaCe_{0.8}Gd_{0.2}Zr_{0.15}O_{3-\alpha}$ | D | C | not measured |
| $Ba_{0.99}Ce_{0.8}Gd_{0.2}Zr_{0.01}O_{3-\alpha}$ | B | A | A |
| $Ba_{0.99}Ce_{0.8}Gd_{0.2}Zr_{0.04}O_{3-\alpha}$ | B | A | A |
| $Ba_{0.99}Ce_{0.8}Gd_{0.2}Zr_{0.06}O_{3-\alpha}$ | B | A | B |
| $Ba_{0.99}Ce_{0.8}Gd_{0.2}Zr_{0.1}O_{3-\alpha}$ | B | A | B |
| $Ba_{0.99}Ce_{0.8}Gd_{0.2}Zr_{0.11}O_{3-\alpha}$ | B | B | C |
| $Ba_{0.98}Ce_{0.8}Gd_{0.2}Zr_{0.01}O_{3-\alpha}$ | B | A | A |
| $Ba_{0.98}Ce_{0.8}Gd_{0.2}Zr_{0.04}O_{3-\alpha}$ | B | A | B |
| $Ba_{0.98}Ce_{0.8}Gd_{0.2}Zr_{0.06}O_{3-\alpha}$ | B | A | B |
| $Ba_{0.98}Ce_{0.8}Gd_{0.2}Zr_{0.1}O_{3-\alpha}$ | B | A | B |
| $Ba_{0.98}Ce_{0.8}Gd_{0.2}Zr_{0.11}O_{3-\alpha}$ | B | B | C |
| $Ba_{0.98}Ce_{0.8}Gd_{0.16}Zr_{0.04}O_{3-\alpha}$ | B | A | B |
| $Ba_{0.98}Ce_{0.8}Gd_{0.23}Zr_{0.04}O_{3-\alpha}$ | B | A | B |
| $Ba_{0.98}Ce_{0.8}Gd_{0.26}Zr_{0.04}O_{3-\alpha}$ | B | A | A |
| $Ba_{0.9}Ce_{0.8}Gd_{0.2}Zr_{0.01}O_{3-\alpha}$ | B | A | B |
| $Ba_{0.9}Ce_{0.8}Gd_{0.2}Zr_{0.04}O_{3-\alpha}$ | B | A | C |
| $Ba_{0.9}Ce_{0.8}Gd_{0.2}Zr_{0.06}O_{3-\alpha}$ | B | A | C |
| $Ba_{0.9}Ce_{0.8}Gd_{0.2}Zr_{0.1}O_{3-\alpha}$ | A | A | C |
| $Ba_{0.9}Ce_{0.8}Gd_{0.2}Zr_{0.11}O_{3-\alpha}$ | A | B | D |
| $Ba_{0.89}Ce_{0.8}Gd_{0.2}Zr_{0.01}O_{3-\alpha}$ | B | A | C |
| $Ba_{0.85}Ce_{0.8}Gd_{0.2}Zr_{0.04}O_{3-\alpha}$ | B | A | D |

TABLE 3

Additive System

| Material | Boiling Test | Crystallinity | Conductivity |
|---|---|---|---|
| $Ba_{0.98}Ce_{0.8}Gd_{0.2}Zr_{0.04}O_{3-\alpha}$ | B | A | B |
| $Ba_{0.99}Ce_{0.8}Gd_{0.2}Zr_{0.01}O_{3-\alpha}$ | B | A | A |
| $Ba_{0.9}Ce_{0.8}Gd_{0.2}Zr_{0.01}O_{3-\alpha}$ | B | A | C |
| $Ba_{0.98}Ce_{0.8}Gd_{0.2}Zr_{0.04}O_{3-\alpha}$ | B | A | C |
| $Ba_{0.99}Ce_{0.8}Gd_{0.2}Zr_{0.01}O_{3-\alpha}$ | B | A | B |
| $Ba_{0.9}Ce_{0.8}Gd_{0.2}Zr_{0.01}O_{3-\alpha}$ | B | A | C |
| $Ba_{0.98}Ce_{0.8}Gd_{0.2}Zr_{0.04}O_{3-\alpha}$ | B | A | B |
| $Ba_{0.99}Ce_{0.8}Gd_{0.2}Zr_{0.01}O_{3-\alpha}$ | B | A | B |
| $Ba_{0.9}Ce_{0.8}Gd_{0.2}Zr_{0.01}O_{3-\alpha}$ | B | A | C |
| $Ba_{0.98}Ce_{0.8}Gd_{0.2}Zr_{0.04}O_{3-\alpha}$ | B | A | B |
| $Ba_{0.99}Ce_{0.8}Gd_{0.2}Zr_{0.01}O_{3-\alpha}$ | B | A | B |
| $Ba_{0.9}Ce_{0.8}Gd_{0.2}Zr_{0.1}O_{3-\alpha}$ | B | A | C |
| $Ba_{0.98}Ce_{0.8}Pm_{0.2}Zr_{0.04}O_{3-\alpha}$ | B | A | B |
| $Ba_{0.99}Ce_{0.8}Pm_{0.2}Zr_{0.01}O_{3-\alpha}$ | B | A | B |
| $Ba_{0.9}Ce_{0.8}Pm_{0.2}Zr_{0.1}O_{3-\alpha}$ | B | A | C |
| $Ba_{0.98}Ce_{0.8}Sm_{0.2}Zr_{0.04}O_{3-\alpha}$ | B | A | B |
| $Ba_{0.99}Ce_{0.8}Sm_{0.2}Zr_{0.01}O_{3-\alpha}$ | B | A | A |

TABLE 3-continued

Additive System

| Material | Boiling Test | Crystallinity | Conductivity |
|---|---|---|---|
| $Ba_{0.9}Ce_{0.8}Sm_{0.2}Zr_{0.1}O_{3-\alpha}$ | B | A | C |
| $Ba_{0.98}Ce_{0.8}Eu_{0.2}Zr_{0.04}O_{3-\alpha}$ | B | A | B |
| $Ba_{0.99}Ce_{0.8}Eu_{0.2}Zr_{0.01}O_{3-\alpha}$ | B | A | A |
| $Ba_{0.9}Ce_{0.8}Eu_{0.2}Zr_{0.1}O_{3-\alpha}$ | B | A | C |
| $Ba_{0.98}Ce_{0.8}Tb_{0.2}Zr_{0.04}O_{3-\alpha}$ | B | A | B |
| $Ba_{0.99}Ce_{0.8}Tb_{0.2}Zr_{0.01}O_{3-\alpha}$ | B | A | A |
| $Ba_{0.9}Ce_{0.8}Tb_{0.2}Zr_{0.1}O_{3-\alpha}$ | B | A | C |
| $Ba_{0.98}Ce_{0.8}Dy_{0.2}Zr_{0.04}O_{3-\alpha}$ | B | A | B |
| $Ba_{0.99}Ce_{0.8}Dy_{0.2}Zr_{0.01}O_{3-\alpha}$ | B | A | A |
| $Ba_{0.9}Ce_{0.8}Dy_{0.2}Zr_{0.1}O_{3-\alpha}$ | B | A | C |
| $Ba_{0.98}Ce_{0.8}Ho_{0.2}Zr_{0.04}O_{3-\alpha}$ | B | A | B |
| $Ba_{0.98}Ce_{0.8}Ho_{0.2}Zr_{0.01}O_{3-\alpha}$ | B | A | B |
| $Ba_{0.9}Ce_{0.8}Ho_{0.2}Zr_{0.1}O_{3-\alpha}$ | B | A | C |
| $Ba_{0.98}Ce_{0.8}Er_{0.2}Zr_{0.04}O_{3-\alpha}$ | B | A | B |
| $Ba_{0.99}Ce_{0.8}Er_{0.2}Zr_{0.01}O_{3-\alpha}$ | B | A | A |
| $Ba_{0.9}Ce_{0.8}Er_{0.2}Zr_{0.1}O_{3-\alpha}$ | B | A | C |
| $Ba_{0.98}Ce_{0.8}Tm_{0.2}Zr_{0.04}O_{3-\alpha}$ | B | A | B |
| $Ba_{0.99}Ce_{0.8}Tm_{0.2}Zr_{0.01}O_{3-\alpha}$ | B | A | B |
| $Ba_{0.9}Ce_{0.8}Tm_{0.2}Zr_{0.1}O_{3-\alpha}$ | B | A | C |
| $Ba_{0.98}Ce_{0.8}Yb_{0.2}Zr_{0.04}O_{3-\alpha}$ | B | A | B |
| $Ba_{0.99}Ce_{0.8}Yb_{0.2}Zr_{0.01}O_{3-\alpha}$ | B | A | A |
| $Ba_{0.9}Ce_{0.8}Yb_{0.2}Zr_{0.1}O_{3-\alpha}$ | B | A | C |

TABLE 4

Additive System

| Material | Boiling Test | Crystallinity | Conductivity |
|---|---|---|---|
| $Ba_{0.99}Ce_{0.8}Gd_{0.2}Ti_{0.01}O_{3-\alpha}$ | B | A | C |
| $Ba_{0.99}Ce_{0.8}Gd_{0.2}Ti_{0.1}O_{3-\alpha}$ | B | A | C |
| $Ba_{0.98}Ce_{0.8}Gd_{0.2}Ti_{0.04}O_{3-\alpha}$ | B | A | C |
| $Ba_{0.9}Ce_{0.8}Gd_{0.2}Ti_{0.1}O_{3-\alpha}$ | A | A | C |
| $Ba_{0.98}Ce_{0.8}Gd_{0.16}Ti_{0.04}O_{3-\alpha}$ | B | A | C |
| $Ba_{0.99}Ce_{0.8}Gd_{0.2}Ti_{0.01}O_{3-\alpha}$ | B | A | A |
| $Ba_{0.98}Ce_{0.8}Gd_{0.2}Ti_{0.1}O_{3-\alpha}$ | B | A | B |
| $Ba_{0.98}Ce_{0.8}Gd_{0.2}Ti_{0.04}O_{3-\alpha}$ | B | A | B |
| $Ba_{0.9}Ce_{0.8}Gd_{0.2}Ti_{0.1}O_{3-\alpha}$ | A | A | C |
| $Ba_{0.98}Ce_{0.8}Gd_{0.16}Ti_{0.04}O_{3-\alpha}$ | B | A | B |
| $Ba_{0.99}Ce_{0.8}Gd_{0.2}Pb_{0.01}O_{3-\alpha}$ | B | A | B |
| $Ba_{0.99}Ce_{0.8}Gd_{0.2}Pb_{0.1}O_{3-\alpha}$ | B | A | C |
| $Ba_{0.98}Ce_{0.8}Gd_{0.2}Pb_{0.04}O_{3-\alpha}$ | B | A | B |
| $Ba_{0.9}Ce_{0.8}Gd_{0.2}Pb_{0.1}O_{3-\alpha}$ | A | A | C |
| $Ba_{0.98}Ce_{0.8}Gd_{0.16}Pb_{0.04}O_{3-\alpha}$ | B | A | C |
| $Ba_{0.99}Ce_{0.8}Gd_{0.2}Ga_{0.01}O_{3-\alpha}$ | B | A | A |
| $Ba_{0.99}Ce_{0.8}Gd_{0.2}Ga_{0.1}O_{3-\alpha}$ | B | A | C |
| $Ba_{0.98}Ce_{0.8}Gd_{0.2}Ga_{0.04}O_{3-\alpha}$ | B | A | B |
| $Ba_{0.9}Ce_{0.8}Gd_{0.2}Ga_{0.1}O_{3-\alpha}$ | A | A | C |
| $Ba_{0.98}Ce_{0.8}Gd_{0.2}Ga_{0.04}O_{3-\alpha}$ | B | A | B |
| $Ba_{0.98}Ce_{0.8}Gd_{0.2}V_{0.04}O_{3-\alpha}$ | C | A | C |
| $Ba_{0.98}Ce_{0.8}Gd_{0.2}Nb_{0.04}O_{3-\alpha}$ | C | A | C |
| $Ba_{0.98}Ce_{0.8}Gd_{0.2}Cr_{0.04}O_{3-\alpha}$ | C | A | C |
| $Ba_{0.98}Ce_{0.8}Gd_{0.2}Mo_{0.04}O_{3-\alpha}$ | C | A | C |
| $Ba_{0.98}Ce_{0.8}Gd_{0.2}W_{0.04}O_{3-\alpha}$ | C | A | C |
| $Ba_{0.98}Ce_{0.8}Gd_{0.2}Fe_{0.04}O_{3-\alpha}$ | B | A | C |
| $Ba_{0.98}Ce_{0.8}Gd_{0.2}Co_{0.04}O_{3-\alpha}$ | B | A | C |
| $Ba_{0.98}Ce_{0.8}Gd_{0.2}Ni_{0.04}O_{3-\alpha}$ | B | A | C |
| $Ba_{0.98}Ce_{0.8}Gd_{0.2}Cu_{0.04}O_{3-\alpha}$ | B | A | B |
| $Ba_{0.98}Ce_{0.8}Gd_{0.2}Ag_{0.04}O_{3-\alpha}$ | C | A | B |
| $Ba_{0.98}Ce_{0.8}Gd_{0.2}Au_{0.04}O_{3-\alpha}$ | C | A | B |
| $Ba_{0.98}Ce_{0.8}Gd_{0.2}Pd_{0.04}O_{3-\alpha}$ | C | A | B |
| $Ba_{0.98}Ce_{0.8}Gd_{0.2}Pt_{0.04}O_{3-\alpha}$ | C | A | B |
| $Ba_{0.98}Ce_{0.8}Gd_{0.2}Sb_{0.04}O_{3-\alpha}$ | B | A | C |
| $Ba_{0.98}Ce_{0.8}Gd_{0.2}Sn_{0.04}O_{3-\alpha}$ | B | A | C |

TABLE 5

Barium-Zirconium System

| Material | Boiling Test | Crystallinity | Conductivity |
|---|---|---|---|
| $BaZr_{0.84}Y_{0.16}O_{3-\alpha}$ | A | A | C |
| $BaZr_{0.8}Y_{0.2}O_{3-\alpha}$ | A | A | C |
| $BaZr_{0.75}Y_{0.25}O_{3-\alpha}$ | A | A | C |
| $BaZr_{0.7}Y_{0.3}O_{3-\alpha}$ | A | A | B |
| $BaZr_{0.65}Y_{0.35}O_{3-\alpha}$ | B | C | not measured |
| $BaZr_{0.8}In_{0.2}O_{3-\alpha}$ | A | A | C |
| $BaZr_{0.7}In_{0.3}O_{3-\alpha}$ | A | A | B |
| $BaZr_{0.95}Gd_{0.05}O_{3-\alpha}$ | A | A | C |
| $BaZr_{0.84}Gd_{0.16}O_{3-\alpha}$ | A | A | C |
| $BaZr_{0.8}Gd_{0.2}O_{3-\alpha}$ | A | A | C |
| $BaZr_{0.75}Gd_{0.25}O_{3-\alpha}$ | A | A | C |
| $BaZr_{0.7}Gd_{0.3}O_{3-\alpha}$ | A | A | B |
| $BaZr_{0.65}Gd_{0.35}O_{3-\alpha}$ | B | C | not measured |
| $BaZr_{0.84}Sc_{0.16}O_{3-\alpha}$ | A | A | C |
| $BaZr_{0.7}Sc_{0.3}O_{3-\alpha}$ | A | A | B |
| $BaZr_{0.84}Bi_{0.16}O_{3-\alpha}$ | B | A | C |
| $BaZr_{0.8}Bi_{0.2}O_{3-\alpha}$ | A | A | C |
| $BaZr_{0.75}Bi_{0.25}O_{3-\alpha}$ | A | A | C |
| $BaZr_{0.7}Bi_{0.3}O_{3-\alpha}$ | A | A | C |
| $BaZr_{0.95}Yb_{0.06}O_{3-\alpha}$ | A | A | C |
| $BaZr_{0.84}Yb_{0.16}O_{3-\alpha}$ | A | A | C |
| $BaZr_{0.8}Yb_{0.2}O_{3-\alpha}$ | A | A | C |
| $BaZr_{0.75}Yb_{0.25}O_{3-\alpha}$ | A | A | C |
| $BaZr_{0.7}Yb_{0.3}O_{3-\alpha}$ | B | A | C |
| $BaZr_{0.84}Dy_{0.16}O_{3-\alpha}$ | B | A | B |
| $BaZr_{0.75}Dy_{0.25}O_{3-\alpha}$ | A | A | C |
| $BaZr_{0.99}La_{0.01}O_{3-\alpha}$ | A | A | C |
| $BaZr_{0.95}La_{0.05}O_{3-\alpha}$ | A | A | C |
| $BaZr_{0.84}La_{0.16}O_{3-\alpha}$ | A | A | C |
| $BaZr_{0.95}Pr_{0.05}O_{3-\alpha}$ | A | A | C |
| $BaZr_{0.84}Pr_{0.16}O_{3-\alpha}$ | A | A | C |
| $BaZr_{0.75}Pr_{0.25}O_{3-\alpha}$ | A | A | B |
| $BaZr_{0.9}Nd_{0.1}O_{3-\alpha}$ | A | A | C |
| $BaZr_{0.84}Nd_{0.16}O_{3-\alpha}$ | A | A | C |
| $BaZr_{0.9}Pm_{0.1}O_{3-\alpha}$ | A | A | C |
| $BaZr_{0.84}Pm_{0.16}O_{3-\alpha}$ | A | A | C |
| $BaZr_{0.84}Sm_{0.16}O_{3-\alpha}$ | A | A | C |
| $BaZr_{0.8}Sm_{0.2}O_{3-\alpha}$ | A | A | C |
| $BaZr_{0.9}Eu_{0.1}O_{3-\alpha}$ | A | A | C |
| $BaZr_{0.82}Eu_{0.18}O_{3-\alpha}$ | A | A | C |
| $BaZr_{0.8}Eu_{0.2}O_{3-\alpha}$ | A | A | B |
| $BaZr_{0.82}Tb_{0.18}O_{3-\alpha}$ | A | A | C |
| $BaZr_{0.8}Ho_{0.2}O_{3-\alpha}$ | A | A | C |
| $BaZr_{0.74}Er_{0.26}O_{3-\alpha}$ | A | A | C |
| $BaZr_{0.72}Tm_{0.28}O_{3-\alpha}$ | A | A | C |
| $BaZr_{0.8}Ga_{0.2}O_{3-\alpha}$ | A | A | C |
| $BaZr_{0.7}Ga_{0.3}O_{3-\alpha}$ | A | A | C |
| $BaZr_{0.8}Sn_{0.2}O_{3-\alpha}$ | A | A | C |
| $BaZr_{0.75}Sn_{0.25}O_{3-\alpha}$ | A | A | C |
| $BaZr_{0.72}Bi_{0.28}O_{3-\alpha}$ | A | A | C |

TABLE 6

Barium Zirconium Cerium System

| Material | Boiling Test | Crystallinity | Conductivity |
|---|---|---|---|
| $BaCe_{0.1}Zr_{0.74}Y_{0.16}O_{3-\alpha}$ | B | A | B |
| $BaCe_{0.2}Zr_{0.64}Y_{0.16}O_{3-\alpha}$ | A | A | C |
| $BaCe_{0.4}Zr_{0.4}Y_{0.2}O_{3-\alpha}$ | B | A | A |
| $BaCe_{0.05}Zr_{0.9}Gd_{0.05}O_{3-\alpha}$ | A | A | C |
| $BaCe_{0.15}Zr_{0.65}Gd_{0.2}O_{3-\alpha}$ | A | A | C |
| $BaCe_{0.4}Zr_{0.4}Gd_{0.2}O_{3-\alpha}$ | B | A | A |
| $BaCe_{0.5}Zr_{0.3}Gd_{0.2}O_{3-\alpha}$ | B | A | A |
| $BaCe_{0.2}Zr_{0.6}Gd_{0.2}O_{3-\alpha}$ | A | A | B |
| $Ba_{0.99}Ce_{0.2}Zr_{0.6}Gd_{0.2}O_{3-\alpha}$ | A | A | B |
| $BaCe_{0.35}Zr_{0.5}Gd_{0.15}O_{3-\alpha}$ | A | A | A |
| $Ba_{0.99}Ce_{0.35}Zr_{0.5}Gd_{0.15}O_{3-\alpha}$ | A | A | A |
| $BaCe_{0.4}Zr_{0.45}Gd_{0.15}O_{3-\alpha}$ | A | A | B |
| $BaCe_{0.4}Zr_{0.5}Gd_{0.1}O_{3-\alpha}$ | A | A | B |
| $BaCe_{0.1}Zr_{0.7}Gd_{0.29}O_{3-\alpha}$ | A | A | C |
| $BaCe_{0.05}Zr_{0.85}Gd_{0.1}O_{3-\alpha}$ | A | A | C |

TABLE 6-continued

Barium Zirconium Cerium System

| Material | Boiling Test | Crystallinity | Conductivity |
|---|---|---|---|
| $BaCe_{0.2}Zr_{0.65}Sc_{0.05}O_{3-\alpha}$ | A | A | C |
| $BaCe_{0.05}Zr_{0.8}Sc_{0.15}O_{3-\alpha}$ | A | A | C |
| $BaCe_{0.05}Zr_{0.85}Bi_{0.1}O_{3-\alpha}$ | A | A | C |
| $BaCe_{0.2}Zr_{0.6}Bi_{0.2}O_{3-\alpha}$ | A | A | C |
| $BaCe_{0.4}Zr_{0.55}Bi_{0.05}O_{3-\alpha}$ | A | A | C |
| $BaCe_{0.05}Zr_{0.7}Bi_{0.25}O_{3-\alpha}$ | A | A | C |
| $BaCe_{0.05}Zr_{0.9}Yb_{0.05}O_{3-\alpha}$ | A | A | C |
| $BaCe_{0.2}Zr_{0.75}Yb_{0.05}O_{3-\alpha}$ | A | A | C |
| $BaCe_{0.4}Zr_{0.4}Yb_{0.2}O_{3-\alpha}$ | B | A | A |
| $BaCe_{0.05}Zr_{0.7}Yb_{0.25}O_{3-\alpha}$ | A | A | C |
| $BaCe_{0.1}Zr_{0.6}Yb_{0.3}O_{3-\alpha}$ | A | A | C |
| $BaCe_{0.05}Zr_{0.8}Dy_{0.15}O_{3-\alpha}$ | A | A | C |
| $BaCe_{0.2}Zr_{0.7}Dy_{0.1}O_{3-\alpha}$ | A | A | C |
| $BaCe_{0.2}Zr_{0.75}La_{0.05}O_{3-\alpha}$ | A | A | C |
| $BaCe_{0.05}Zr_{0.85}La_{0.05}O_{3-\alpha}$ | A | A | |
| $BaCe_{0.4}Zr_{0.4}La_{0.2}O_{3-\alpha}$ | A | A | C |
| $BaCe_{0.2}Zr_{0.75}Pr_{0.05}O_{3-\alpha}$ | A | A | C |
| $BaCe_{0.4}Zr_{0.5}Pr_{0.1}O_{3-\alpha}$ | B | A | C |
| $BaCe_{0.2}Zr_{0.7}Nd_{0.1}O_{3-\alpha}$ | A | A | C |
| $BaCe_{0.4}Zr_{0.45}Nd_{0.05}O_{3-\alpha}$ | B | A | B |
| $BaCe_{0.4}Zr_{0.4}Nd_{0.2}O_{3-\alpha}$ | B | A | B |
| $BaCe_{0.4}Zr_{0.4}Pm_{0.2}O_{3-\alpha}$ | B | A | C |
| $BaCe_{0.4}Zr_{0.5}Pm_{0.1}O_{3-\alpha}$ | B | A | C |
| $BaCe_{0.4}Zr_{0.5}Sm_{0.1}O_{3-\alpha}$ | B | A | B |
| $BaCe_{0.1}Zr_{0.7}Sm_{0.2}O_{3-\alpha}$ | A | A | C |
| $BaCe_{0.4}Zr_{0.4}Eu_{0.2}O_{3-\alpha}$ | B | A | B |
| $BaCe_{0.4}Zr_{0.5}Eu_{0.1}O_{3-\alpha}$ | B | A | C |
| $BaCe_{0.4}Zr_{0.4}Eu_{0.2}O_{3-\alpha}$ | B | A | C |
| $BaCe_{0.4}Zr_{0.55}Tb_{0.05}O_{3-\alpha}$ | B | A | C |
| $BaCe_{0.05}Zr_{0.8}Ho_{0.15}O_{3-\alpha}$ | A | A | C |
| $BaCe_{0.5}Zr_{0.4}Er_{0.1}O_{3-\alpha}$ | B | A | C |
| $BaCe_{0.5}Zr_{0.35}Tm_{0.15}O_{3-\alpha}$ | B | A | C |
| $BaCe_{0.4}Zr_{0.4}Ga_{0.2}O_{3-\alpha}$ | B | A | C |
| $BaCe_{0.05}Zr_{0.7}Ga_{0.25}O_{3-\alpha}$ | A | A | C |
| $BaCe_{0.1}Zr_{0.8}Sn_{0.1}O_{3-\alpha}$ | A | A | C |
| $BaCe_{0.05}Zr_{0.75}Sn_{0.2}O_{3-\alpha}$ | A | A | C |
| $BaCe_{0.4}Zr_{0.4}Sb_{0.2}O_{3-\alpha}$ | B | A | C |
| $BaCe_{0.4}Zr_{0.4}In_{0.2}O_{3-\alpha}$ | B | A | A |
| $Ba_{0.99}Ce_{0.4}Zr_{0.4}In_{0.2}O_{3-\alpha}$ | B | A | A |
| $BaCe_{0.2}Zr_{0.6}In_{0.2}O_{3-\alpha}$ | A | A | B |
| $BaCe_{0.3}Zr_{0.5}In_{0.2}O_{3-\alpha}$ | A | A | A |
| $BaCe_{0.4}Zr_{0.4}In_{0.1}O_{3-\alpha}$ | A | A | A |
| $BaCe_{0.5}Zr_{0.4}In_{0.1}O_{3-\alpha}$ | A | A | A |
| $BaCe_{0.5}Zr_{0.3}In_{0.2}O_{3-\alpha}$ | A | A | A |
| $BaCe_{0.5}Zr_{0.3}In_{0.1}O_{3-\alpha}$ | B | A | A |

As becomes clear from this evaluation, mixed ionic conductors in accordance with the present invention have considerably better moisture resistance, while the ion conductivity can be held at a practical level.

The above examples have been synthesized by solid state sintering, but there is no limitation to this method, and the oxide also can be synthesized by coprecipitation, nitration, spray granulation or any other suitable method. It is also possible to use film forming methods such as CVD or sputtering methods. It is also possible to use thermal spraying. There is no limitation to the shape of the oxide, and it can be of any shape, including bulk shapes and films.

The invention may be embodied in other specific forms without departing from the spirit or essential characteristics thereof. The embodiments disclosed in this application are to be considered in all respects as illustrative and not restrictive, the scope of the invention being indicated by the appended claims rather than by the foregoing description, all changes that come within the meaning and range of equivalency of the claims are intended to be embraced therein.

What is claimed is:

1. A mixed ionic conductor comprising an ion conductive oxide having a perovskite structure of the formula $Ba_dZr_{1-x-y}Ce_xM^3{}_yO_{3-\gamma}$ wherein $M^3$ is at least one element selected from the group consisting of Sm, Eu, Gd, Tb, Yb, Y, Sc and In; with
$0.98 \leq d \leq 1$;
$0.01 \leq x < 0.5$;
$0.01 \leq y \leq 0.3$; and
$(2+y-2d)/2 \leq \gamma < 1.5$.

2. The mixed ionic conductor of claim 1, wherein $M^3$ is selected from the group consisting of Gd, In, Y and Yb.

3. A fuel cell comprising as a solid-state electrolyte a mixed ionic conductor of claim 1.

4. A gas sensor comprising as a solid-state electrolyte a mixed ionic conductor of claim 1.

5. The mixed ionic conductor of claim 1, wherein d=1.

6. The mixed ionic conductor of claim 1, wherein $0.01 \leq x \leq 0.4$.

* * * * *